United States Patent

Hidaka et al.

[11] Patent Number: 5,609,672
[45] Date of Patent: Mar. 11, 1997

[54] COMPOSITION FOR COLOR DEVELOPMENT COMPRISING 4-HYDROXY-4'-ISOPROPOXYDIPHENYLSULFONE, AND A WET METHOD FOR GRINDING AND A DISPERSIBLE SOLUTION FOR APPLYING THE SAME

[75] Inventors: Tomoya Hidaka; Shinichi Sato, both of Yusyudai-Higashi; Hiroyasu Sato, Iwaki; Yutaka Takashina, Takahagi, all of Japan

[73] Assignee: Nippon Soda Co., Ltd., Tokyo, Japan

[21] Appl. No.: 495,442

[22] PCT Filed: Dec. 26, 1994

[86] PCT No.: PCT/JP94/02221

§ 371 Date: Jul. 26, 1995

§ 102(e) Date: Jul. 26, 1995

[87] PCT Pub. No.: WO95/18018

PCT Pub. Date: Jul. 6, 1995

[30] Foreign Application Priority Data

Dec. 27, 1993 [JP] Japan .................................... 5-348443

[51] Int. Cl.$^6$ ............................................. C09D 11/02
[52] U.S. Cl. ........................................ 106/21 R; 106/21 A
[58] Field of Search ............................... 106/21 A, 21 R; 568/34; 503/216

[56] References Cited

U.S. PATENT DOCUMENTS 4,556,687  12/1985  Maierson .................... 106/21 R
4,614,757  9/1986   Maierson .................... 106/21 R
5,024,699  6/1991   Llyama et al. ............... 106/21 R

FOREIGN PATENT DOCUMENTS 003990  1/1988  Japan .
076779  3/1990  Japan .
135788  5/1992  Japan .

*Primary Examiner*—Helene Klemanski
*Attorney, Agent, or Firm*—Joseph C. Mason, Jr.; Louise A. Foutch

[57] ABSTRACT

A method for preventing the generation of the hydration of 4-hydroxy-4'-isopropoxydiphenylsulfone characterized in that the particles of 4-hydroxy-4'-isopropoxydiphenylsulfone are subjected to wet grinding in water in the presence of diphenylsulfone derivatives represented by the general formula (I);

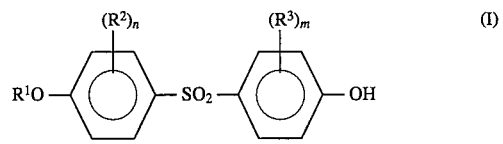

wherein $R^1$ represents hydrogen or lower alkyl, $R^2$ and $R^3$ represent each independently lower alkyl, n and m denote 0 or an integer of from 1 to 4, with a proviso that n and m can never be 0 at the same time in case $R^1$ represents hydrogen, is disclosed. By using the dispersible solution of color developer according to the present invention, the production of high sensitive and unclean background-free thermal sensitive recording papers can be accomplished.

6 Claims, No Drawings

COMPOSITION FOR COLOR DEVELOPMENT COMPRISING 4-HYDROXY-4'-ISOPROPOXYDIPHENYLSULFONE, AND A WET METHOD FOR GRINDING AND A DISPERSIBLE SOLUTION FOR APPLYING THE SAME

FIELD OF THE INVENTION

The present invention relates to 4-hydroxy-4'-isopropoxydiphenylsulfone which can function as a color developer to be used for the production of recording papers such as thermal sensitive recording papers.

BACKGROUND ART

In the manufacturing of thermal sensitive recording papers, a leuco chlomogen and a color developer, which are both colorless or pale-colored, are normally coated on supporting materials such as papers. In the process for the manufacturing of a coating solution for such use, a color developer is dispersed into an aquatic solution of water-soluble polymer being a binding agent to prepare the coating solution. Since thermal sensitive recording papers are required to have a property of high sensitivity to temperature, it is necessary to make the particle size of a color developer in the dispersible solution thereof fine as much as possible in order to produce thermal sensitive recording papers having excellent temperature-sensitive property. For this reason, most of dispersible solutions of color developers wherein a color developer is grinded up to fine particles, have been produced by adding the color developer into an aquatic solution of a water-soluble polymer and subsequently grinding them throughly by employing certain wet grinding method.

Although 4-hydroxy-4'-isopropoxydiphenylsulfone can function as an excellent color developer and has been widely used, the compound sometimes develops crystals thereof either during the process of wet grinding to prepare a dispersible solution of the color developer or during the preservation of the dispersible solution of the color developer prepared, if the color developer was grinded up to fine particles by employing the means as described above. Particularly, this phenomenon becomes more conspicuous when 4-hydroxy-4'-isopropoxydiphenylsulfone is grinded up to a particle size of less than 1 μm. It is understood that this development of crystals is brought as a result of hydration phenomenon of 4-hydroxy-4'-isopropoxydiphenylsulfone and the crystals developed are the hydrate of 4-hydroxy-4'-isopropoxydiphenylsulfone. This hydrate seriously relates to a disadvantageous property of thermal sensitive recording papers such as unclean background, because the thermal sensitive recording papers tend to result in uncleanness of the background of the recording papers if they are produced in using a dispersible solution of a color developer which contains such hydrate.

As a means for preventing the generation of said crystal development (hydration), a method to add 4,4'-dihydroxydiphenylsulfone into 4-hydroxy-4'-isopropoxydiphenylsulfone to thereby prevent the generation of crystals development, is disclosed in Japanese Patent Laid-opened No. Hei 2-76779. By even employing this method for the production of thermal sensitive recording papers, however, the recording papers frequently give said unclean background when the adding rate of 4-4'-dihydroxydiphenylsulfone is raised to 5% more or less.

It is an object of the present invention to provide an improved means for preventing the generation of said hydration of 4-hydroxy-4'-isopropoxydiphenyls ulfone in the process of the production of a dispersible solution of color developer and during the storing thereof.

DISCLOSURE OF THE INVENTION

It is an object of the present invention to provide a method for preventing the generation of the hydration of 4-hydroxy-4'-isopropoxydiphenylsulfone by contaminating therein a compound selected from a group consisting of diphenylsulfone derivatives represented by the general formula (I);

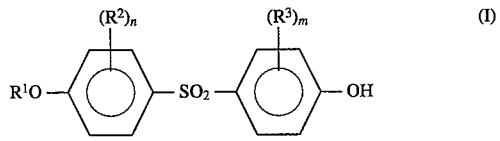

wherein $R^1$ represents hydrogen or lower alkyl, $R^2$ and $R^3$ represent each independently lower alkyl, n and m denote 0 or an integer of from 1 to 4, with a proviso that n and m can never be 0 at the same time in case $R^1$ represents hydrogen, in an amount of 0.01 part by weight or more in respect to 100 parts by weight of 4-hydroxy-4'-isopropoxydiphenylsulfone.

It is a further object of the present invention to provide a composition for color development comprising 4-hydroxy-4'-isopropoxydiphenylsulfone which further contains a diphenylsulfone derivative represented by the general formula (I) and to provide a dispersible solution comprising said composition for color development.

It is a still further object of the present invention to provide a wet method for grinding 4-hydroxy-4'-isopropoxydiphenylsulfone in water characterized in that the particles of 4-hydroxy-4'-isopropoxydiphenylsulfone are subjected to wet grinding in the presence of at least one compound selected from a group consisting of diphenylsulfone derivatives represented by the general formula (I).

The lower alkyl which can be exemplified for the substituents $R^1$, $R^2$ and $R^3$ in diphenylsulfone derivatives represented by the general formula (I), are methyl, ethyl, propyl, isopropyl, n-butyl, sec-butyl, tert-butyl, etc.

Now, the representative compounds for diphenylsulfone derivatives represented by the general formula (I) which contain the lower alkyl substituents as exemplified above are recited hereinbelow. In the examples of the representative compounds recited below, propyl and isopropyl are represented by isopropyl; n-butyl, isobutyl, sec-butyl and tert-butyl are altogether represented by n-butyl.

4-hydroxy-3-methyl-4'-isopropoxydiphenylsulfone
4-hydroxy-3-ethyl-4'-isopropoxydiphenylsulfone
4-hydroxy-3-isopropyl-4'-isopropoxydiphenylsulfone
4-hydroxy-3-n-butyl-4'-isopropoxydiphenylsulfone
4-hydroxy-3'-methyl-4'-isopropoxydiphenylsulfone
4-hydroxy-3'-ethyl-4'-isopropoxydiphenylsulfone
4-hydroxy-3'-isopropyl-4'-isopropoxydiphenylsulfone
4-hydroxy-3'-n-butyl-4'-isopropoxydiphenylsulfone
4-hydroxy-3-methyl-4'-methoxydiphenylsulfone
4-hydroxy-3-ethyl-4'-methoxydiphenylsulfone
4-hydroxy-3-isopropyl-4'-methoxydiphenylsulfone
4-hydroxy-3-isopropyl-4'-ethoxydiphenylsulfone
4-hydroxy-3-isopropyl-4'-n-butoxydiphenylsulfone
4-hydroxy-3-n-butyl-4'-methoxydiphenylsulfone
4-hydroxy-3,3'-dimethyl-4'-methoxydiphenylsulfone
4-hydroxy-2,2'-dimethyl-4'-isopropoxydiphenylsulfone
4-hydroxy-3,3'-dimethyl-4'-isopropoxydiphenylsulfone
4-hydroxy-3,3',5,5'-tetramethyl-4'-methoxydiphenylsulfone 4-hydroxy-3,3',5,5'-tetramethyl-4'-isopropoxydiphenylsulfone
4, 4'-dihydroxy-2-methyldiphenylsulfone
4, 4'-dihydroxy-2-ethyldiphenylsulfone
4, 4'-dihydroxy-2-isopropyldiphenylsulfone
4, 4'-dihydroxy-2-n-butyldiphenylsulfone
4, 4'-dihydroxy-3-methyldiphenylsulfone
4, 4'-dihydroxy-3-ethyldiphenylsulfone
4, 4'-dihydroxy-3-isopropyldiphenylsulfone
4, 4'-dihydroxy-3-n-butyldiphenylsulfone
4, 4'-dihydroxy-3, 3'-dimethyldiphenylsulfone
4, 4'-dihydroxy-3, 3'-diethyldiphenylsulfone
4, 4'-dihydroxy-3, 3'-diisopropyldiphenylsulfone
4, 4'-dihydroxy-2, 2'-dimethyldiphenylsulfone
4, 4'-dihydroxy-2, 2'-diethyldiphenylsulfone
4, 4'-dihydroxy-2, 2'-diisopropyldiphenylsulfone
4, 4'-dihydroxy-2, 2'-diisobutyldiphenylsulfone
4, 4'-dihydroxy-3, 3', 5, 5'-tetramethyldiphenylsulfone
4, 4'-dihydroxy-3, 3', 5, 5'-tetraethyldiphenylsulfone
4, 4'-dihydroxy-3, 3', 5, 5'-tetraisopropyldiphenylsulfone The content of a diphenylsulfone derivative represented by the general formula (I) in the dispersible solution is 0.01 part by weight or more in respect to 100 parts by weight of 4-hydroxy-4'-isopropoxydiphenylsulfone. However, it is preferable that said content of the diphenylsulfone derivative is 0.05 part by weight or more in order to prevent the generation of the hydration of 4-hydroxy-4'-isopropoxydiphenylsulfone in the dispersible solution for color development prepared by wet grinding. Furthermore, it is required that said content of the diphenylsulfone derivative is 0.10 part by weight or more in order to ensure complete prevention of the generation of the hydration of 4-hydroxy-4'-isopropoxydiphenylsulfone in the dispersible solution for color development throughout the long-term preservation thereof. Although said preventing effect can be obtained as well when the content of the diphenylsulfone derivative is more than 1.0 part by weight, and even 5.0 parts by weight or more, it will not give any further advantage in the property and is just uneconomic. Considering the practical use of the dispersible solution, it is preferable to fix the content in a range of from 0.05 to 1.0 part by weight, and more preferably in a range of from 0.1 to 0.6 part by weight, in respect to 100 parts by weight of 4-hydroxy-4'-isopropoxydiphenylsulfone.

The diphenylsulfone derivative represented by the general formula (I) is added to 4-hydroxy-4'-isopropoxydiphenylsulfone to be contained therein. At the addition, the diphenylsulfone derivative in either forms of powder or solution in a solvent can be alternatively added to the reactant solution or into the crystals of 4-hydroxy-4'-isopropoxydiphenylsulfone precipitated during the manufacturing of 4-hydroxy-4'-isopropoxydiphenylsulfone. Furthermore, the diphenylsulfone derivative can be added to the dispersible solution of 4-hydroxy-4'-isopropoxydiphenylsulfone at adjusting the solution just before subjecting it to the wet grinding process. If 4-hydroxy-4'-isopropoxydiphenylsulfone is synthesized by the reaction of 4,4'-dihydroxydiphenylsulfone and isopropylbromide, there would be the generation of a diphenylsulfone derivative represented by the general formula (I) as by-product. In such case, it is possible to leave the by-product there to utilize as a diphenylsulfone derivative required for the addition described above and to further add supplemental quantity of fresh diphenylsulfone derivative if the amount of the by-product generated therein is not enough for obtaining the sufficient preventive effect. When plural types of the diphenylsulfone derivatives represented by the general formula (I) are generated as by-products, all of the derivatives generated can be used in the same manner as described above.

Although water is employed as a dispersing carrier for the wet grinding specified in the present invention, it is preferable to carry out the wet grinding in the presence of a dispersing agent in order to improve the dispersibility of 4-hydroxy-4'-isopropoxydiphenylsulfone in the dispersible solution. As dispersing agents described above, dispersing agents or surface active agents normally used can be employed. However, for the production of thermal sensitive recording papers, it is a common procedure to prepare a dispersible solution of a color developer in a state of fine particles by dispersing the color developer into a solution of water-soluble polymer to be used as a binder and subjecting the resulting mixture to the subsequent wet grinding process. In the present invention, it is also preferable to use said water-soluble polymer as a dispersing agent then proceeding to the subsequent wet grinding process.

For the water-soluble polymers, compounds to be used as binders for color developers, such as polyvinyl alcohol, methylcellulose, carboxymethylcellulose, hydroxyethylcellulose, polyacrylamide and starch, can be exemplified. Among them, polyvinyl alcohol is the most common compound for such use. However, it is possible to add other additives normally used for a dispersible solution of a color developer into a dispersing carrier.

The wet grinding method specified in the present invention does not require any particular conditions, so that normal wet grinding methods using ball mill, sand mill, etc. can be employed in the present invention. There is no particular requirement for the concentration range of 4-hydroxy-4'-isopropoxydiphenylsulfone in the composition for color development when it is subjected to the wet grinding, and therefore the wet grinding can be operated at any concentration of 4-hydroxy-4'-isopropoxydiphenylsulfone as far as the concentration is adequate for a coating solution used for the production of thermal sensitive recording papers.

The formation of the hydrates can be determined by several means, such as IR spectrum, differential thermal analysis, etc. On the other hand, microscopical observation on the dispersible solution can be utilized as a simple method for the determination, since the crystals of 4-hydroxy-4'-isopropoxydiphenylsulfone develop to rough and large in size and become visible as the hydration of the particles thereof is going on.

BEST MODE FOR CARRYING OUT THE PRESENT INVENTION

Now, the present invention is further explained in detail by referring the examples. However, the scope of the present invention shall not be limited to the descriptions in the following examples.

EXAMPLE 1

31.1 g of 15% aqueous solution of polyvinyl alcohol, 30 g of pure water, 195 g of glass beads (1.0–1.5 mmø), 13.9 g of 4-hydroxy-4'-isopropoxydiphenylsulfone and 0.014 g of 4-hydroxy-3-isopropyl-4'-isopropoxydiphenylsulfone (adding ratio: 0.10% by weight) were each weighed and mixed altogether, then the mixture was subjected to wet grinding at 25° C. by using a wet grinder (Manufactured by Igarashi Machinery Manufacturing Co., Ltd.; Trade name, Sandgrinder). On microscopical observation, crystal development in the mixture was seen after 3 hours from the start of the wet grinding. The average particle size in the mixture after the wet grinding was 0.5 μm according to the measurement by using laser diffraction-type particle size distribution analyzer (Shimazu Particle Size Distribution Analyzer SALD-1000, at 50% average particle size).

EXAMPLE 2

By employing the same procedure as described in the example 1 except the replacement of the dose of 4-hydroxy-3-isopropyl-4'-isopropoxydiphenylsulfone from 0.014 g (adding ratio: 0.10% by weight) to 0.028 g (adding ratio: 0.20% by weight), wet grinding was carried out. On microscopical observation, no crystal development in the mixture was detected even after 10 hours from the start of the wet grinding. The average particle size in the mixture after the wet grinding was 0.3 μm according to the measurement by using the same method described in the Example 1.

EXAMPLE 3

By employing the same procedure as described in the example 2 except the replacement of from 4-hydroxy-3-isopropyl-4'-isopropoxydiphenylsulfone to 4, 4'-dihydroxy-3-isopropyldiphenylsulfone, wet grinding was carried out. On microscopical observation, no crystal development in the mixture was detected even after 10 hours from the start of the wet grinding. The average particle size in the mixture after the wet grinding was 0.3 μm according to the measurement by using the same method described in the Example 1.

COMPARATIVE EXAMPLE

With no addition of the compound of the present invention, wet grinding was carried out according to the same procedure as described in the example 1. On microscopical observation, clear crystal development in the mixture was seen after 1 hour from the start of the wet grinding. The average particle size in the mixture after the wet grinding was 0.8 μm according to the measurement by using the same method described in the Example 1. Incidentally, in the example 1 above, the average particle size in the grinded mixture after 1 hour was 0.5 μm.

INDUSTRIAL APPLICABILITY

The sensitivity of thermal sensitive recording papers and carbonless papers tend to be improved as the particle size of a color developer to be coated on the papers is made finer.

According to the present invention, a dispersible solution comprising 4-hydroxy-4'-isopropoxydiphenylsulfone in a state of very fine particles can be easily prepared, because the present invention enables the wet grinding which can make the particles of 4-hydroxy-4'-isopropoxydiphenylsulfone fine up to an extent of less than 1 μm in the average particle size without causing the hydration of the compound and the particles grinded do not generate the hydration in the dispersible solution prepared as well.

Therefore, the production of high sensitive and unclean background-free thermal sensitive recording papers can be accomplished by using the dispersible solution of color developer according to the present invention.

What is claimed is:

1. A composition for color development comprising 4-hydroxy-4'-isopropoxydiphenylsulfone wherein the composition contains at least one compound selected from the group consisting of diphenylsulfone derivatives represented by formula (I):

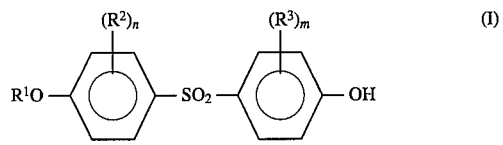

wherein $R^1$ represents hydrogen or lower alkyl, $R^2$ and $R^3$ each independently represent a lower alkyl, n and m are 0 or an integer of from 1 to 4, with the proviso that n and m are not both 0, in an amount in total ranging from 0.05 to 5.0 parts by weight in respect to 100 parts by weight of 4-hydroxy-4'-isopropoxydiphenylsulfone.

2. A method for preventing the generation of the hydration of 4-hydroxy-4'-isopropoxydiphenylsulfone comprising adding at least one compound selected from the group consisting of diphenylsulfone derivatives represented by formula (I);

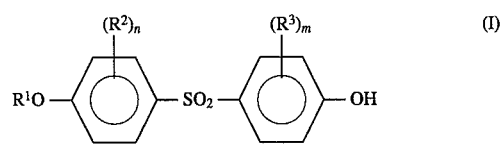

wherein $R^1$ represents hydrogen or lower alkyl, $R^2$ and $R^3$ each independently represent a lower alkyl, n and m are 0 or an integer of from 1 to 4, with the proviso that n and m are not both 0, in an amount in total ranging from 0.05 to 5.0 parts by weight in respect to 100 parts by weight of 4-hydroxy-4'-isopropoxydiphenylsulfone to a dispersible solution of 4-hydroxy-4'-isopropoxydiphenylsulfone.

3. A method for grinding or dispersing 4-hydroxy-4'-isopropoxydiphenylsulfone in a dispersing carrier without generating the hydration thereof, comprising subjecting particles of 4-hydroxy-4'-isopropoxydiphenylsulfone to a wet grinding process or dispersion in the presence of at least one compound selected from the group consisting of diphenylsulfone derivatives represented by formula (I);

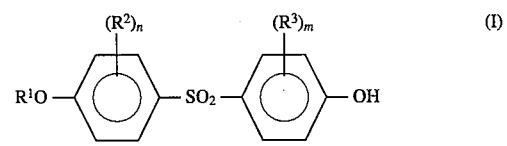

wherein $R^1$ represents hydrogen or lower alkyl, $R^2$ and $R^3$ each independently represent a lower alkyl, n and m are 0 or an integer of from 1 to 4, with the proviso that n and m are not both 0, in an amount ranging from 0.05 to 5.0 parts by weight in respect to 100 parts by weight of 4-hydroxy-4'-isopropoxydiphenylsulfone.

4. A method for grinding 4-hydroxy-4'-isopropoxydiphenylsulfone comprising subjecting a composition for color development according to the claim 1 to a wet grinding process.

5. A dispersible solution wherein a composition for color development according to claim 1 is dispersed in water.

6. The method for grinding or dispersing 4-hydroxy-4'-isopropoxydiphenylsulfone according to claim 3 wherein the amount in total of the at least one compound selected from the group consisting of diphenylsulfone derivatives represented by formula (I);

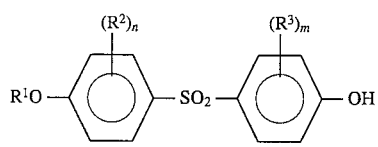 (I)
is in a range of from 0.05 to 1.0 part by weight in respect to 100 parts by weight of 4-hydroxy-4'-isopropoxydiphenyl-sulfone.
* * * * *